United States Patent [19]

Shansky

[11] Patent Number: 5,350,424
[45] Date of Patent: Sep. 27, 1994

[54] DYESTUFF COMPOSITION FOR THE GRADUAL DYEING OF HAIR BY ATMOSPHERIC OXIDATION AND PROCESS USING THE SAME

[75] Inventor: Albert Shansky, Norwalk, Conn.

[73] Assignee: Combe Incorporated, White Plains, N.Y.

[21] Appl. No.: 959,343

[22] Filed: Oct. 13, 1992

[51] Int. Cl.$^5$ ................................. A61K 7/13
[52] U.S. Cl. ................................. 8/406; 8/408; 8/409; 8/421
[58] Field of Search ............ 8/406, 408, 409, 410, 8/421, 423; 424/70

[56] References Cited

U.S. PATENT DOCUMENTS

| | | | |
|---|---|---|---|
| 305,057 | 9/1884 | De Barbaran | 8/405 |
| 1,019,576 | 3/1912 | Wolfenstein | 8/405 |
| 2,185,467 | 1/1940 | Kritchevsky | 167/88 |
| 2,934,396 | 4/1960 | Charle | 8/11 |
| 3,128,232 | 4/1964 | Wilmsmann et al. | 167/88 |
| 3,792,090 | 2/1974 | Kalopissis et al. | 260/571 |
| 3,871,818 | 3/1975 | Kinney et al. | 8/10.2 |
| 3,899,288 | 8/1975 | Galerne | 8/10.2 |
| 3,920,384 | 11/1975 | Feinland et al. | 8/10.2 |
| 4,008,043 | 2/1977 | Kalopissis | 8/10.2 |
| 4,008,999 | 2/1977 | Kalopissis et al. | 8/10.2 |
| 4,054,413 | 10/1977 | Feinland et al. | 8/10.2 |
| 4,104,020 | 8/1978 | Rose | 8/10.2 |
| 4,104,021 | 8/1978 | Lapidus et al. | 8/10.2 |
| 4,297,098 | 10/1981 | Dasher et al. | 8/412 |
| 4,381,920 | 5/1983 | Garlen | 8/406 |
| 4,529,404 | 7/1985 | Feinland et al. | 8/406 |
| 4,695,285 | 9/1987 | Chung-Bong-Chan et al. | 8/405 |
| 5,021,067 | 6/1991 | Grollier | 8/409 |
| 5,073,174 | 12/1991 | Vayssie et al. | 8/406 |
| 5,100,436 | 3/1992 | Wenke | 8/405 |

FOREIGN PATENT DOCUMENTS

| | | |
|---|---|---|
| 3246747 | 12/1982 | Fed. Rep. of Germany . |
| 1290299 | 9/1972 | United Kingdom ............ F16F 1/06 |
| 2105754 | 3/1983 | United Kingdom . |

OTHER PUBLICATIONS

The Chemistry and Manufacture of Cosmetics, 2nd E., vol. IV by deNavarre, published by Continental Press, 1975, pp. 856-889.

*Primary Examiner*—Paul Lieberman
*Assistant Examiner*—Caroline L. Dusheck
*Attorney, Agent, or Firm*—Fitzpatrick, Cella, Harper & Scinto

[57] ABSTRACT

A dyestuff composition for gradually dyeing hair by atmospheric oxidation wherein the dyestuff composition contains a dye component which becomes entrapped in hair fibers when the dyestuff composition is removed from the hair and which results in the gradual development of color in the hair due to atmospheric oxidation of the entrapped dye component. Also provided is a process of employing the dyestuff composition of this invention to gradually dye hair, the dyestuff composition being removed from the hair approximately 5 minutes after its application.

13 Claims, No Drawings

DYESTUFF COMPOSITION FOR THE GRADUAL DYEING OF HAIR BY ATMOSPHERIC OXIDATION AND PROCESS USING THE SAME

BACKGROUND OF THE INVENTION

1. Field of the Invention

The invention relates to a dyestuff composition for gradually dyeing hair by atmospheric oxidation wherein an adherent dyestuff composition contains a dye component which becomes entrapped in hair fibers when the dyestuff composition is rinsed from the hair and which results in the gradual development of color in the hair due to atmospheric oxidation of the entrapped dye component. The invention also relates to a process of employing the aforementioned dyestuff composition to gradually dye hair.

2. Background Art

The dyeing of human hair with dyestuff compositions containing an oxidizable dye component is well known. The overwhelming majority of commercial hair dyes employ an oxidizable dye component and a chemical oxidizing agent in an amount which causes a prompt reaction and results in a predetermined target color 30 minutes after application. For instance, U.S. Pat. No. 3,649,159 discloses a hair dyeing process involving application to hair of a dyestuff composition containing primary intermediates, such as oxidizable primary aromatic amines (especially diamines) and substitution products thereof, usually together with aminophenols, in admixture with an oxidizing agent—especially $H_2O_2$ or its derivatives, such as urea peroxide, perborates, percarbonates, persulfates, perphosphates, periodares or the like—whereby so-called oxidation dyes are formed in situ on the hair. In the color-forming reaction, the aromatic primary amino groups and phenolic hydroxyl groups are oxidized in situ to form imino groups and CO groups, and coupling occurs to form polyimino compounds in which the aromatic nuclei assume a quinonoid-like configuration.

It is customary also to include as part of the dye component, color coupling compounds such as a polyhydric phenol—e.g. resorcinol, pyrogallol or the like.

The color reaction of a mixture of a primary intermediate, such as p-phenylene diamine, and a color coupler, such as m-phenylene diamine, is illustrative. First, the p-phenylene diamine is oxidized to p-benzoquinone diimine. Thereafter, there are two simultaneous reactions, one of which is the self-coupling of the p-benzoquinone diimine to produce a brown-colored Bandrowski's base. The other is the reaction of p-benzoquinone with m-phenylene diamine to produce an indamine dye of blue-purple color. By the addition of other primary intermediates and other color couplers to the reaction mixture it is possible to produce additional colored molecular species so that the final color can be adjusted to that which is desired.

Typically, a dyestuff component, comprising primary intermediates and couplers, is solubilized in a suitable carrier at about a 1% concentration. The carrier can be made sufficiently alkaline, typically above pH 9.5, so as to release oxygen from the peroxide salt and accelerate oxidation. It has been found such treatment also swells the hair imbrications or scales so that the carrier and dye component can penetrate the hair fiber.

In general, at least a molecular equivalent or in excess thereof of an oxidizing reagent, relative to the oxidizable diamine or aminophenol, is employed, although somewhat lesser proportions of oxidant can be used. While it is known that atmospheric oxygen can be utilized in hair dyeing, the use of added oxidizing agents has been widely preferred, since the color-forming reaction proceeds more rapidly in the presence of oxidizing agents and the target color can be more readily achieved. Generally the oxidizing agent, such as a peroxide, is kept separate from the dye component and is added just prior to application to the hair. The advantage of oxidizing the primary intermediate and color couplers after they have penetrated the hair fiber is that the final dye molecules are larger than either starting reactant. Thus, the larger dye molecules become trapped in the hair fibers and the coloration produced thereby is very resistant to washing.

Typically, the reaction between a dyestuff composition and an oxidizing agent requires 20 to 40 minutes for a target color to be developed. Thereafter, the unreacted dyestuff is removed from the hair by water rinsing or shampooing. Such compositions have been conventionally combined with conventional hair care surfactants (detergents, wetting agents), so as to facilitate removal of unreacted dye component by rinsing. During rinsing, surfactants and wetting agents routinely employed in commercial dyestuff compositions promote the removal of unreacted dye components that have penetrated the hair fiber, as well the composition left on the surface of the hair. Thus, rinsing commercial dyestuff compositions from the hair essentially terminates the hair color process.

Other types of known oxidative dyes include the derivatives of 4,7-diaminoindazole disclosed by U.S. Pat. No. 4,104,020. These derivatives in combination with a color coupler are oxidized by atmospheric oxygen to give color in a relatively short time, although the use of a chemical oxidizing agent is preferred.

Also known are hair dyeing compositions containing leuco derivatives of indoanilines, such as the diphenylamines disclosed in U.S. Pat. No. 3,792,090, U.S. Pat. No. 4,008,403 and U.S. Pat. No. 4,008,999. The leuco derivatives, which are, by definition, colorless compounds, are oxidized to their corresponding indolamines by either atmospheric oxygen or an oxidizing agent such as hydrogen peroxide and are said to give better reproducible shades than can be obtained with primary dye intermediates and color couplers. The leuco derivatives tend to form the colored indolamine compound shortly after application, e.g., within 20 minutes, even when oxidized solely by atmospheric oxygen.

Commercial hair dyestuff compositions for women generally employ a dyeing process in which the target color is attained in a single treatment—usually involving application of colorant mixture and oxidant in suitable proportions for the desired target color, allowing the development reaction to proceed for 15 to 60 minutes to develop the desired color followed by washing the hair. Men, however, are usually reluctant to dye their hair such that a complete color change occurs in a single treatment, since they find this accelerated color change undesirable.

A number of preparations have been marketed for men which gradually change or darken hair color by repeated applications of the dyeing composition at selected intervals, and maintenance of the final desired coloration is effected by further applications at less frequent intervals. Gradual darkening of hair has been produced by repeated application of an air oxidation dye color mixture which is left on the hair as a hair grooming composition. The hair is not rinsed or shampooed after application, and atmospheric oxygen is relied upon to develop the coloration, as disclosed, for example, by U.S. Pat. Nos. 3,920,384 and 4,054,413. This method, although widely used, may be improved by reducing the time the composition is left on the hair since certain users do not like to leave the composition on the hair.

It was also known to modify the depth of shade by varying the concentration of the colorant, as taught by U.S. Pat. Nos. 305,057, 1,019,576, 2,185,467, 3,128,232 and Br. Patent No. 12,902/99, not only with oxidation color mixtures, but also with pyro-gallo-Ni salt mixtures and direct dyes. Depth of shade has also been controlled by increasing the duration of the treatment, utilizing phthalaldehyde combined with an alkylolamine as the colorant mixture, as disclosed by U.S. Pat. No. 3,871,818. It is also known, as disclosed in U.S. Pat. No. 4,104,021, to gradually dye hair by successive treatments of the hair with aromatic primary amines in which the concentration of added oxidizing agent is increased at each successive application. After applying the mixture to the hair, color generally develops in from 5 to 15 minutes.

Another method of obtaining gradual coloring of hair employs a low concentration of oxidative dye components (preferably 0.2 to 0.5% by weight) in which most of color development is obtained by atmospheric oxidation within 30 to 60 minutes of application of the preparation, as disclosed by U.S. Pat. No. 4,297,098. The preparation used in this prior art method is to be left on the hair. After 30 to 60 minutes most of the color change is said to occur. This and other formulations containing air oxidizable dyestuffs usually contain surfactants and wetting agents. Upon rinsing, such additives remove any unoxidized dye component from the hair, so that atmospheric oxidation color development is essentially terminated upon rinsing.

Thus, conventional dye formulations, even those containing air-oxidizable dye components, remove unreacted dyestuff components from the hair upon washing via the presence of the surfactants. Further, such formulations seek to develop a target color in a relatively short time after application and cannot tolerate any long term uncontrolled reactions which develop deeper shades.

Accordingly, it is an object of this invention to provide a composition for causing a gradual coloration in the hair over an extended period of time by application of a dyestuff composition to the hair, promptly fixing the dyestuff in the hair fibers and then removing unfixed dyestuff from the surface of the hair.

It is another object to slowly and imperceptibly develop a desired coloration in the hair by applying dyestuff composition, and rinsing to fix the dyestuff within about 5 minutes after application, wherein no color change is perceptible after unfixed dyestuff is removed.

SUMMARY OF THE INVENTION

The present invention is an air-oxidizable dyestuff composition for gradually dyeing hair by atmospheric oxidation wherein the dyestuff composition is an adherent or sticky gel containing a dye component which becomes entrapped in hair fibers with the aid of the sticky gel. The entrapped dye component is fixed in the hair fibers, when the dyestuff composition is rinsed from the hair. Any remaining dye component is removed from the surface of the hair by shampooing or the like. Gradual development of color in the hair occurs due to atmospheric oxidation of the fixed dye component. In addition, this invention includes a process of employing the instant dyestuff composition to gradually dye hair over a period generally from 24 to 72 hours. Satisfactory results are obtained when the dyestuff is fixed and excess dyestuff removed from the surface of the hair after a targeted time, usually, after about 5 minutes from the time of application with color becoming perceptible in 24 to 72 hours. This result is unexpected because conventional expertise dictates that insufficient dye would remain in the hair after the dyestuff composition is removed by rinsing and shampooing.

The air-oxidizable dye component in gel form is adapted to penetrate the hair fibers when applied at an elevated alkaline pH, and to become entrapped in the hair shafts to fix the dye component therein, when the dyestuff composition is removed from the hair after a targeted time, usually on the order of 5 minutes or less. The absence of surfactants or wetting agents in the air-oxidizable dyestuff composition allows the entrapped dye component to remain in the hair fibers in spite of the subsequent rinsing and shampooing steps. This is an important feature of the present invention, since it was expected that rinsing and shampooing would remove so much dye component that no color would develop.

The dyestuff composition and process of this invention can also be used incrementally to gradually reach a desired target color of the treated hair. The dyestuff composition and process of this invention are particularly advantageous for dyeing hair in a gradual manner that is not startling or overly obvious to others and that does not require leaving the dyestuff composition on the hair for extended periods of time.

The adherent gel dyestuff composition for the gradual dyeing of hair by atmospheric oxidation comprises (i) an air-oxidizable dye component and (ii) a carrier, the adherent gel dyestuff composition having a pH sufficiently alkaline to allow the dye component to penetrate hair fibers after application thereto, the dyestuff composition containing a sufficient amount of the dye component to cause a portion of the dye component to adhere and become fixed in said hair fibers when the hair is rinsed before a color is perceived and any remaining dye component being readily removed from the hair surface, whereby gradual development of color in the hair occurs due to atmospheric oxidation of the fixed dye component.

It should be understood that the air-oxidizable dye component employed in this invention does not develop visually perceivable color before the excess dyestuff composition is removed from the hair. Moreover, the dyestuff composition of the present invention does not require the presence of any chemical oxidizing agent, since color is developed primarily through atmospheric oxidation. The dye composition of this invention is constituted so that it may be applied to the hair and then removed typically within about 5 minutes after application.

Accordingly, dye components which tend to oxidize promptly are not preferably employed in the invention. Diphenylamine dyes, such as disclosed in U.S. Pat. No. 3,792,090, are quickly oxidized to produce color shortly after application and do not gradually dye the hair over a long period of time by air oxidation.

In the present invention, the high pH of the inventive composition raises the hair imbrications. The coloring material in sticky gel form is then deposited within the hair shaft and locked in by the rinsing step which closes the imbrications. The viscous, sticky gel form of the composition aids in entrapping the dye component within the hair shaft so that the rinsing step will close the imbrications and so fix the dye component in the hair that subsequent shampooing will not wash it out. That the fixed dye component remains entrapped even when exposed to surfactant-containing shampoos designed to remove excess coloring material is quite surprising.

The hair is shampooed to remove excess coloring material from the surface of the hair fiber. Hair color does not result at this time. Hair color appears only after oxygen in the air reacts with the entrapped coloring material; usually in 24 to 72 hours. The hair is left clean and free of excess material. This eliminates color rub-off. Such gradual dyeing of the hair is desirable to those persons, especially men, who prefer visually undetected incremental hair dyeing.

The dyestuff composition of this invention has a sufficiently alkaline pH to allow the dye component to penetrate the hair fibers. Penetration of the hair fibers is facilitated by the alkaline medium which causes the hair to swell and raises the imbrications or scales of the hair.

Furthermore, sufficient adherent dyestuff component in gel form is present to permit the dye component to become entrapped and fixed in the hair fibers during water rinsing so that an ostensible color will result after the atmospheric oxidative development period. To this end, the gel dyestuff composition of this invention is especially adherent to the hair since it is substantially free of those surfactants and wetting agents typically employed in commercial hair dyeing compositions designed to remove dye components from hair fibers during water rinsing. That the dye component remains fixed in the hair fibers after rinsing and shampooing is an unexpected feature of this invention, since such treatment was expected to remove so much of the dye component as to prevent coloring.

The invention also includes a process for gradually dyeing hair by atmospheric oxidation with an adherent gel dyestuff composition having a carrier and an air-oxidizable dye component comprising the steps of:

(a) applying the adherent gel dyestuff composition to the surface of the hair, the dyestuff composition (i) having a pH sufficiently alkaline to penetrate hair fibers and (ii) containing a sufficient amount of the air-oxidizable dye component to allow the dye component to be deposited in the hair fibers;

(b) rinsing the hair to fix the deposited dye component in the hair fibers; and (c) removing any remaining dyestuff composition from the surface of the hair, whereby gradual development of color in the hair occurs due to atmospheric oxidation of said fixed dye component.

As previously noted the rinsing step closes the hair imbrications to fix the deposited dye component and the removal step (as by shampooing) eliminates any dye component present on the hair surface to prevent rub-off.

The process may be repeated as necessary to reach a target color by incrementally dyeing the hair. Each dyeing cycle causes more dye to be entrapped in the hair shafts and a deeper shade to develop. Thereafter, the target color may be maintained by periodic applications of the dyestuff composition. The rinsing step is conducted in a predetermined time after applying the dyestuff composition to the hair. In general, the rinsing step is conducted within about 5 minutes from application.

It has been found that the inventive composition and dyeing process which causes the dye to be locked in the hair fibers produces a highly lustrous and deep coloration. The invention provides a unique dye composition and process in which (1) dye components are easy to apply in a short period of time; (2) a slow, barely perceptible change to a targeted color can be readily achieved; (3) a high degree of coverage can be provided for gray hair; (4) dye application is non-staining to hands and scalp; (5) the fixed composition resists rub-off and wear-off; and (6) the fixed dye is fast to light, perspiration and shampoo.

DETAILED DESCRIPTION OF THE INVENTION

The air-oxidizable dye component contained in the dyestuff composition of the present invention preferably includes one or more primary intermediates, such as oxidizable primary aromatic amines or aminophenols. The primary intermediates will form a dye by themselves upon oxidation. Typical oxidizable para- and ortho-aromatic primary amines and aminophenols include: o- and p-phenylenediamine; 2-amino-4-nitrophenol; 4-amino-2-nitrophenol; o- and p-aminophenol; o- and p-methylaminophenol; 2-aminophenol-4-sulfonic acid; 4-aminophenol-2-sulfonic acid; o-anisidine; 2,4-diaminoanisole; 2,5-diaminoanisole; 1,8-diaminonaphthalene; 2,4-diaminophenol; 2,4-diaminophenetol; 2,5-diaminophenol-4-sulfonic acid; N,N'-dimethyl-p-phenylenediamine; 4,6-dinitro-2-aminophenol; N-(p-hydroxyphenyl)-glycine; N-(2-hydroxy-5-nitrophenyl)-glycine; p-methylaminophenol; 4-nitro-o-phenylenediamine; 2,4,6-trinitroaniline; p-toluylenediamine; 6-nitro-2,4,diaminophenol; 2,4,6-triaminophenol; 2,5-diaminophenol; 6-hydroxy-1,2,4,triaminobenzene; 3,4-diaminophenol; 2,5-diaminohydro-quinone; 4-N-dimethylaminocatechol; 4-methoxy-o-phenylenediamine; 2,4,6-trihydroxyaniline; 5-amino-1,2,3-trihydroxybenzene; 4-N,N-diethylaminobenzene; 2-amino-1,5-dihydroxynaphthalene; 5-hydroxy-6,8-diaminoquinoline and 2,3,6-triaminopyridine.

The dye component can also be employed in a water-soluble salt form, such as a sulfate, hydrochloride, acetate or the like. One or more of such primary intermediates may be present in the dyestuff composition of this invention.

Particularly preferred primary intermediates of this invention include p-phenylene diamine, 2,4-diaminophenetol sulfate and N-phenyl-p-phenylene diamine.

The air-oxidizable dye component may also contain one or more color couplers, such as m-diamines, m-amino phenols, mono- and poly-hydric phenols and naphthols The couplers are especially useful for providing specific color effects or to stabilize color when employed with the primary intermediates. Illustrative examples of color couplers which may be employed in the dye component of the present invention include: α-naphthol, o-cresol, m-cresol, 2,6-dimethylphenol, 2,5-dimethylphenol, 3,4-dimethylphenol, 3,5-dimethylphenol, pyrocatechol, pyrogallol, 1,5-dihydroxy naphthalene, 1,7-dihydroxy napthalene, 5-amino-2-methylphenol, hydroquinone, 2,4-diaminoanisole, m-toluylenediamine, 4-aminophenol, resorcinol, 4- chlororesorcinol, resorcinol monomethyl ether (3-methoxyphenol), m-phenylenediamine, 3-methyl-1-phenyl-5-pyrazolone, 3-amino-1-phenyl-5-pyrazolone, 1-phenyl-3,5-dionepyrazolidine, 7-(dimethylamino)-4-hydroxy-1-methyl-2-quinolone, 1-amino-3-(acetacetylamino)-4-nitrobenzene, and 1-amino-3-(cyanoacetylamino)-4-nitrobenzene. One or more of the color couplers may be present in the dyestuff composition.

Particularly preferred color couplers include resorcinol, 4-chlororesorcinol and m-aminophenol.

In general, especially rapid diffusion of the dye component into the hair occurs when dye molecules have a diameter of less than about 6 Å, although larger molecules can be employed on the order of 10 Å with slower diffusion. To provide enhanced diffusion, both the diameter of the molecules and the pH of the composition can be adjusted as required.

As noted above, the dye component may include one or more primary intermediates along with one or more color couplers. The final color and hue obtained may be adjusted by varying the combination of primary intermediates and color couplers employed in the dye component. Such variation of the constituent primary intermediates and color couplers making up the dye component is well within the knowledge of those skilled in the hair dyeing art. The instant dye composition can provide light to darker brown shades, yellow shades and the like. The various primary intermediates and couplers also contribute blue, magenta and purple hues which are useful in adjusting final hair color. Accordingly, the preferred combination of primary intermediates and color couplers making up the dye component of this invention is limited only by the final hair color desired from the dyestuff composition of this invention. Warm shades, dark shades and fashion shades may be targeted.

In general, the air-oxidizable dye component is present in amounts sufficient to penetrate the hair fibers, to remain entrapped in the hair shafts upon rinsing, to resist removal by the shampooing step which washes off excess surface dye component, and to provide perceptible color after gradual atmospheric oxidation. For this and other purposes, the total amount of dye component is present in amounts from about 0.5 to 3.5% w/w. Unless indicated otherwise, all weights are based on the total weight of the dyestuff composition. Enhanced results are obtained, and accordingly it is preferred to employ from about 1.0 to 2.7% w/w of the dyestuff component.

When a combination of primary intermediates and color couplers is employed as the dyestuff component the weight ratio of primary intermediate to color couplers is usually from about 12:1 to 1:1, preferably 9:1 to 2.0:1.

If desired the primary intermediate may be the sole dyestuff component. In that event generally from about 0.5 to 3.0% w/w is employed.

It is a feature of the invention that the dyestuff composition does not develop any visually perceptible color even as it is removed from the hair shortly after application. Typically, the dyestuff composition is rinsed from the hair at a targeted time, about 5 minutes after application. However, longer or shorter application times are also feasible, as long as no color is perceived prior to rinsing and a perceptible color gradually develops in the hair after rinsing over a period of from about 24 to 72 hours. In general, the hair is shampooed or otherwise treated to remove the dye component present on the surface of the hair.

Of course, prompt removal of the dyestuff composition from the hair is particularly advantageous, since the shorter the application time, the more convenient and practicable the dyestuff composition. For example, the composition can be applied in the morning prior to shaving and removed after shaving. The composition can be applied periodically until the desired color is achieved.

The dyestuff composition of this invention has a sufficiently alkaline pH to cause the dye component to penetrate hair fibers after application thereto. For this and other purposes, the dyestuff composition preferably has a pH of at least about 9 and no greater than about 11 and, most preferably, from 9.5 to 10.5. The dyestuff composition is made sufficiently alkaline, as required, by the inclusion of alkaline agents in the dyestuff composition. Illustrative alkaline agents for adjusting the pH include ammonia; alkanolamines, such as mono-, di- and triethanolamine; water soluble alicyclic amines, such as morpholine; and alkali metal salts of weak inorganic acids such as borax, alkali metal sulfites, alkali metal phosphates and alkali metal carbonates. Preferably, the alkaline agent is monoethanolamine, which is usually present in amounts from 1.0 to 3.0% w/w, and, preferably, from 1.5 to 2.5% w/w.

The dyestuff composition of this invention relies upon oxygen in the atmosphere to oxidize the dye component which is entrapped in the hair fibers. Accordingly, chemical oxidizing agents are not required in the coloring composition. Added oxidizers can cause premature color to appear and defeat the purpose of the instant composition which is to provide an imperceptible, gradual hair coloration. (However, for some purposes it may be acceptable to employ minor amounts of oxidants if some immediate coloration is acceptable.)

An aqueous carrier is preferably employed as the vehicle in the dyestuff composition. More preferably, deionized water is employed as the carrier. The aqueous carrier can also contain conventional solvents including: lower alcohols, such as ethyl alcohol, propyl or isopropyl alcohol, and tert-butyl alcohol; glycols, such as ethylene glycol and propylene glycol; glycol ethers, such as ethylene glycol monomethyl or monobutyl ether, ethylene glycol monoethyl ether acetate, propylene glycol and dipropylene glycol monomethyl ether; methyl lactate and the like. In general, the aqueous carrier is employed in broad amounts. For best results from about 80–90%, more preferably, about 82–88% w/w water is employed.

The composition is preferably employed in a sticky, viscous gel form to assist in entrapping the dye component in the hair shaft. To provide the composition with desired viscosity, thickeners may be employed. Typical thickening agents include: sodium alginate; gum arabic; guar or carob gum; heterobiopolysaccharides, such as xanthan gum; cellulose derivatives, such as methyl cellulose, hydroxyethylcellulose, hydroxymethylcellulose, hydroxypropylcellulose and carboxymethylcellulose; and various polymers having thickening functions, such as acrylic acid derivatives.

The thickening agent preferably employed in the inventive compositions is "Carbopol 941" (tradename of B.F. Goodrich Company), a polymer of acrylic acid crosslinked with a polyfunctional agent such as triethanolamine. The thickening agents are preferably present in amounts between 0.2 and 3.0% w/w, and especially between 0.5 and 1.5% w/w.

The dyestuff compositions of this invention may also contain compatible adjuvants well known in hair dyeing including: antioxidants, such as erythorbic acid and sodium sulfite; and conditioning agents and fragrances, provided that the composition functions as described herein. An aerosol form or a mousse form of the composition can also be utilized.

The process of this invention includes, preferably, initially shampooing the hair to remove all excess debris. Thereafter, the dyestuff composition is applied to the hair. Preferably, the dye composition has been thickened by the inclusion of one or more thickening agents. The thickened dyestuff composition is then combed through the hair. The composition is left on the hair for a short period of time, preferably no longer than about 5 minutes. After about 5 minutes, and before any color is visually perceived, the dyestuff composition is removed from the hair. This may be accomplished by rinsing the hair to cause the hair imbrications to close and to fix the deposited colorant. Thereafter, the hair can be shampooed to wash out the remaining dyestuff composition on the surface of the hair.

A sufficient amount of air-oxidizable dye component is employed in the adherent dyestuff composition when practicing the process to cause the dye component to be so entrapped in the hair fibers when the hair is rinsed, that a target color is obtained after the oxidative development period. The purpose of the rinse is to ensure that the air-oxidizable dye component which has penetrated the hair fiber is entrapped. The subsequent shampoo treatment removes the composition left on the surface of the hair shaft. This leaves the surface of the hair completely clean and free of any excess material. Thereafter, gradual development of color in the hair occurs due to atmospheric oxidation of said entrapped dye component, generally resulting in an ostensible color after approximately 24 to 72, and usually 24 to 48 hours. If little or no excess dye component remains on the surface of the hair after rinsing, the shampooing step can be eliminated.

Further treatments with the dyestuff composition may be undertaken after the color is developed. In this manner successive treatments are conducted until a final target color is reached. Thereafter, the target color is maintained by periodic treatments with the dyestuff composition.

The examples which follow are intended as an illustration of certain preferred embodiments of the invention, and no limitation of the invention is implied. In the following examples, all amounts are in percent by weight of the total composition.

EXAMPLE 1

The following dyestuff composition was prepared:

| Composition | Amount |
| --- | --- |
| Water | 84.578 |
| Carbopol 941 ® | 1.000 |
| Erythorbic acid | 0.500 |
| Sodium sulfite | 0.200 |
| 4-chlororesorcinol | 0.299 |
| P-phenylenediamine | 1.518 |
| 2,4-Diaminophenetol sulfate | 0.299 |
| N-phenyl-p-phenylenediamine | 0.506 |
| Triethanolamine (99%) | 8.600 |
| Fragrance | 0.500 |

-continued

| Composition | Amount |
| --- | --- |
| Monoethanolamine | 2.000 |

The hair was first shampooed and then the composition was applied to the hair and combed through. The composition was allowed to dwell for about 5 minutes. The hair was water rinsed and then shampooed again. After the rinse no color was perceived on the hair. An ostensible, but pale dark brown shade appeared on the hair in about 24 hours.

EXAMPLE 2

The following dyestuff composition was prepared:

| Composition | Amount |
| --- | --- |
| Water | 85.556 |
| Carbopol 941 ® | 1.000 |
| Erythorbic acid | 0.500 |
| Sodium sulfite | 0.200 |
| 4-chlororesorcinol | 0.608 |
| P-phenylenediamine | 0.608 |
| 2,4-Diaminophenetol sulfate | 0.185 |
| N-phenyl-p-phenylenediamine | 0.203 |
| M-aminophenol | 0.040 |
| Triethanolamine (99%) | 8.600 |
| Fragrance | 0.500 |
| Monoethanolamine | 2.000 |

The hair was first shampooed and then the composition was applied to the hair and combed through. The composition was allowed to dwell for about 5 minutes. The hair was water rinsed and then shampooed again. After the rinse no color was perceived on the hair. An ostensible, but pale medium brown shade appeared on the hair in about 24 hours.

EXAMPLE 3

The following dyestuff composition was prepared:

| Composition | Amount |
| --- | --- |
| Water | 86.150 |
| Carbopol 941 ® | 1.000 |
| Erythorbic acid | 0.500 |
| Sodium sulfite | 0.200 |
| Resorcinol | 0.450 |
| P-phenylenediamine | 0.400 |
| 2,4-Diaminophenetol sulfate | 0.200 |
| Triethanolamine (99%) | 8.600 |
| Fragrance | 0.500 |
| Monoethanolamine | 2.000 |

The hair was first shampooed and then the composition was applied to the hair and combed through. The composition was allowed to dwell for about 5 minutes.

The hair was water rinsed and then shampooed again. After the rinse no color was perceived on the hair. An ostensible, but pale light brown shade appeared on the hair in about 24 hours.

EXAMPLE 4

The dyestuff composition of Example 1 is reapplied in the same manner as in Example 1 after the color has developed from the prior application. The depth of color of the dark brown shade in the hair is enhanced in about 24 hours.

EXAMPLE 5

The dyestuff composition of Example 2 is reapplied in the same manner as in Example 2 after the color has developed from the prior application. The depth of color of the medium brown shade on the hair is enhanced in about 24 hours.

EXAMPLE 6

The dyestuff composition of Example 3 is reapplied in the same manner as in Example 3 after the color has developed from the prior application. The depth of color of the light brown shade on the hair is enhanced in about 24 hours.

EXAMPLE 7

A dyestuff composition is prepared by adding Carbopol 941 ® and triethanolamine to a deionized water solution of 2.0% w/w p-phenylenediamine to thicken the composition to a desired degree. Next, a monoethanolamine aqueous solution is added to the thickened dyestuff composition until a pH of about 10.0 is obtained.

Thereafter, hair is shampooed and the dyestuff composition is applied to the hair and combed through. The composition is allowed to dwell for about 5 minutes. The hair is water rinsed and then shampooed again. After the rinse no color is perceived on the hair. An ostensible, but pale brown shade appears on the hair in about 24 hours.

Other variations and modifications of this invention will be obvious to those skilled in this art. This invention is not be limited except as set forth in the following claims.

What is claimed is:

1. A process for gradually dyeing hair by atmospheric oxidation with an adherent gel dyestuff composition having an aqueous carrier and an air-oxidizable dye component, wherein said air-oxidizable dye component is an oxidizable primary aromatic amine or an aminophenol, and said adherent gel dyestuff composition is substantially free of surfactants and wetting agents, comprising the steps of:
   (a) applying said adherent gel dyestuff composition to the surface of the hair, said dyestuff composition (i) having a pH of at least about 9 to penetrate hair fibers and (ii) containing a sufficient amount of said air-oxidizable dye component to allow said dye component to be deposited in said hair fibers;
   (b) rinsing the hair to fix the deposited dye component in the hair fibers; and
   (c) removing any remaining dyestuff composition from the surface of the hair, whereby gradual development of color in the hair occurs subsequent to said rinsing due to atmospheric oxidation of said deposited fixed dye component over a period of approximately 24 to 72 hours and being substantially free of chemical oxidants.

2. The process according to claim 1, wherein said rinsing step is performed no longer than about 5 minutes after the application of said dyestuff composition to the hair.

3. The process according to claim 1, wherein said air-oxidizable dye component includes a color coupler selected from the group consisting of m-diamines, m-amino phenols, mono- and poly-hydric phenols and naphthols.

4. The process according to claim 1, wherein said air oxidizable dye component is present in amounts from 0.5 to 3.5% by weight of the total composition.

5. The process according to claim 1, wherein the pH is from about 9.5 to 10.5.

6. The process according to claim 1, wherein said dyestuff composition includes at least one alkaline agent selected from the group consisting of ammonia, alkanolamines, water soluble alicyclic amines, alkali metal salts, alkali metal sulfites, alkali metal phosphates and alkali metal carbonates.

7. The process according to claim 1, wherein said air-oxidizable dye component contains an effective amount of (i) at least one primary intermediate selected from the group consisting of p-phenylenediamine, 2,4-diaminophenetol sulfate and N-phenyl-p-phenylenediamine, and (ii) at least one color coupler selected from the group consisting of 4-chloro resorcinol, resorcinol, and m-aminophenol, to cause an ostensible color in the hair after said atmospheric oxidation.

8. The process according to claim 7, wherein said air-oxidizable dyestuff composition contains an effective amount of monoethanolamine to cause said dye component to penetrate the hair fibers.

9. The process for gradually reaching a desired target color by repeating the process of claim 1 until the desired target color is obtained.

10. The process according to claim 1, wherein the remaining air-oxidizable dye component is removed from the surface of said hair fibers by shampooing.

11. A process for gradually dyeing hair by atmospheric oxidation with an adherent gel dyestuff composition having a carrier, a thickening agent and an air-oxidizable dye component, wherein said adherent gel dyestuff composition is substantially free of surfactants and wetting agents, comprising the steps of:
   (a) applying said adherent gel dyestuff composition containing (i) a primary aromatic amine or aminophenol dye component present in amounts from 0.5 to 3.5% by weight of the total composition to the surface of the hair, said dyestuff composition having a pH from about 9 to 11 to allow said dye component to penetrate hair fibers and to be deposited in said hair fibers and (iii) said thickening agent in amounts sufficient to make said dye component adhere to said hair fibers;
   (b) rinsing the hair to fix the deposited dye component in the hair fibers; and
   (c) removing any remaining dyestuff composition from the surface of the hair, whereby gradual development of color in the hair occurs subsequent to said rinsing due to atmospheric oxidation of said deposited fixed dye component over a period of approximately 24 to 72 hours and being substantially free of chemical oxidants.

12. The process according to claim 1, wherein said air-oxidizable dye component is present in amounts from about 1.0 to 3.5% by weight of the total composition and wherein said air-oxidizable dye component is (a) selected from the group consisting of oxidizable primary aromatic amines, aminophenols and mixtures thereof and (b) optionally includes at least one color coupler.

13. The process according to claim 11, wherein said air-oxidizable dye component is present in amounts from about 1.0 to 3.5% by weight of the total composition and wherein said air-oxidizable dye component is (a) selected from the group consisting of oxidizable primary aromatic amines, aminophenols and mixtures thereof and (b) optionally includes at least one color coupler.

* * * * *

UNITED STATES PATENT AND TRADEMARK OFFICE
CERTIFICATE OF CORRECTION

PATENT NO. : 5,350,424
DATED : September 27, 1994
INVENTOR(S) : Albert Shansky

Page 1 of 2

It is certified that error appears in the above-indentified patent and that said Letters Patent is hereby corrected as shown below:

COLUMN 1

Line 33, "periodares" should read --periodates--.

COLUMN 6

Line 58, "naphthols" should read --naphthols.--.

COLUMN 11

Line 57, "deposited fixed" should read --fixed deposited--.

COLUMN 12

Line 1, "air" should read --air- --.
Line 17, "consisting" should read --consisting of--.

UNITED STATES PATENT AND TRADEMARK OFFICE
CERTIFICATE OF CORRECTION

PATENT NO. : 5,350,424
DATED : September 27, 1994
INVENTOR(S) : Albert Shansky

It is certified that error appears in the above-indentified patent and that said Letters Patent is hereby corrected as shown below:

COLUMN 12

Line 41, "(iii)" should read --(ii)--.
Line 50, "deposited fixed" should read --fixed deposited--.

Signed and Sealed this

Tenth Day of October, 1995

Attest:

BRUCE LEHMAN

Attesting Officer      Commissioner of Patents and Trademarks